US006879856B2

(12) United States Patent
Stadler et al.

(10) Patent No.: US 6,879,856 B2
(45) Date of Patent: Apr. 12, 2005

(54) METHOD AND APPARATUS FOR DETECTION AND TREATMENT OF TACHYCARDIA AND FIBRILLATION

(75) Inventors: Robert W. Stadler, Shoreview, MN (US); Bruce D. Gunderson, Plymouth, MN (US); Jeffrey M. Gillberg, Coon Rapids, MN (US); Walter H. Olson, North Oaks, MN (US)

(73) Assignee: Medtronic, Inc., Minneapolis, MN (US)

( * ) Notice: Subject to any disclaimer, the term of this patent is extended or adjusted under 35 U.S.C. 154(b) by 117 days.

(21) Appl. No.: 09/814,251

(22) Filed: Mar. 21, 2001

(65) Prior Publication Data

US 2001/0034539 A1 Oct. 25, 2001

Related U.S. Application Data

(60) Provisional application No. 60/191,075, filed on Mar. 21, 2000.

(51) Int. Cl.[7] .............................................. A61N 1/368
(52) U.S. Cl. ........................................................ 607/14
(58) Field of Search ................................ 600/509, 515, 600/516, 518, 519, 521; 607/4, 5, 7, 8, 9, 14, 15, 25

(56) References Cited

U.S. PATENT DOCUMENTS

| | | | |
|---|---|---|---|
| 4,375,817 A | 3/1983 | Engle et al. | 128/419 D |
| 4,384,585 A | 5/1983 | Zipes | 128/419 D |
| 4,548,209 A | 10/1985 | Wielders et al. | 128/419 D |
| 4,577,633 A | 3/1986 | Berkovits et al. | 128/419 PG |
| 4,587,970 A | 5/1986 | Holley et al. | 128/419 PG |
| 4,693,253 A | 9/1987 | Adams | 128/419 D |
| 4,726,380 A | 2/1988 | Vollmann et al. | 128/419 PG |
| 4,727,380 A | 2/1988 | Miura et al. | 346/108 |
| 4,800,883 A | 1/1989 | Winstrom | 128/419 D |
| 4,819,643 A | 4/1989 | Menken | 128/419 PG |
| 4,830,006 A | 5/1989 | Haluska et al. | 128/419 PG |
| 4,880,004 A | 11/1989 | Baker, Jr. et al. | 128/419 PG |
| 4,880,005 A | 11/1989 | Pless et al. | 128/419 PG |
| 4,949,719 A | 8/1990 | Pless et al. | 128/419 D |
| 4,949,730 A | 8/1990 | Cobben et al. | 128/775 |
| 4,953,551 A | 9/1990 | Mehra et al. | 128/419 D |
| 4,969,465 A | 11/1990 | Pless et al. | 128/419 |
| 4,971,058 A | 11/1990 | Pless et al. | 128/419 PG |
| 5,117,824 A | 6/1992 | Keimel | 128/419 D |
| 5,163,427 A | 11/1992 | Keimel | 128/419 D |
| 5,188,105 A | 2/1993 | Keimel | 128/419 D |
| 5,312,443 A * | 5/1994 | Adams et al. | 607/5 |
| 5,330,508 A * | 7/1994 | Gunderson | 607/14 |
| 5,464,430 A * | 11/1995 | Rossing | 607/4 |
| 5,855,593 A * | 1/1999 | Olson et al. | 607/9 |

OTHER PUBLICATIONS

Olson et al, "Onset & Stability for Ventricular Tachyarrhythmia Detection in an Implantable Pacer–Cardioverter–Defibrillator" Oct. 7–10, 1986, pp. 167–170 *Computers in Cardiology* IEEE Computer Society Press.

\* cited by examiner

*Primary Examiner*—George R. Evanisko
*Assistant Examiner*—Frances P. Oropeza
(74) *Attorney, Agent, or Firm*—Girma Wolde-Michael; Daniel G. Chapik

(57) ABSTRACT

The invention relates to devices that detect and/or treat tachyarrhythmias. The invention includes software systems that distinguish among various tachyarrhythmias in order to provide treatment for specific tachyarrhythmias. One aspect of the invention employs a methodology to provisionally detect ventricular tachycardia and/or fibrillation and thereafter apply a discrimination function to a series of measured intervals preceding the provisional detection. Discrimination is accomplished by sorting the intervals preceding provisional detection into bins corresponding to interval ranges and examining the relative distribution of the intervals within the bins.

8 Claims, 10 Drawing Sheets

Figure 8a: A scatterplot of arrhythmias from the Performance Evaluation Database and the performance of the New Discrimination for the case with the minimum short interval threshold (120 ms).

Figure 8b: A scatterplot of arrhythmias from Algorithm Development Database and the design of the New Discriminator for the case with the minimum short interval threshold (120 ms).

Figure 8c: Performance of New Discriminator on the Performance Evaluation Database when the short interval threshold was 240 ms.

METHOD AND APPARATUS FOR DETECTION AND TREATMENT OF TACHYCARDIA AND FIBRILLATION

This application claims the benefit of U.S. Provisional Application Ser. No. 60/191,075, filed Mar. 21, 2000, entitled "Method and Apparatus for Detection and Treatment of Tachycardia and Fibrillation," which is incorporated herein by reference in its entirety.

FIELD OF THE INVENTION

This invention relates to devices which detect and/or treat tachyarrhythmias (rapid heart rhythms), and more specifically, to devices and methods to distinguish among various tachyarrhythmias and to provide appropriate therapies to treat the identified tachyarrhythmias.

BACKGROUND OF THE INVENTION

Prior art automatic tachyarrhythmia detection systems for automatic cardioverter/defibrillators rely upon the presence or absence of electrical and mechanical heart activity, such as intramyocardial pressure, blood pressure, impedance, stroke volume or heart movement, for example, and/or the rate of the electrocardiogram to detect hemodynamically compromising ventricular tachycardia or fibrillation.

In pacemaker/cardioverter/defibrillators presently in clinical evaluation, fibrillation is distinguished from ventricular tachycardia using rate based criteria, In such devices, it is generally common to specify the rate or interval ranges that characterize a tachyarrhythmia as opposed to fibrillation. However, some patients may suffer from ventricular tachycardia and ventricular fibrillation that have similar or overlapping rates, making it difficult to distinguish low rate fibrillation from high rate tachycardia. In addition, ventricular fibrillation may display R-R intervals which may vary considerably, resulting in intervals that may fall within both the tachycardia and fibrillation rate or interval ranges, or outside both.

Current pacemaker/cardioverter/defibrillator arrhythmia control devices, such asthose commercially available from Medtronic, Inc., typically employ programmable fibrillation interval ranges and tachycardia detection interval ranges which are adjacent to one another. In the Medtronic devices in particular, the interval range designated as indicative of fibrillation consists of intervals less than a programmable interval (FDI) and the interval range designated as indicative of ventricular tachycardia consists of intervals less than a programmable interval (TDI) and greater than or equal to FDI. R-R intervals falling within these ranges are measured and counted to provide a count (VTEC) of R-R intervals falling within the tachycardia interval range and a count (VFEC) of the number of intervals which fall within the fibrillation interval range, out of a preceding series of a predetermined number (FEB) of intervals. VTEC is incremented in response to R-R intervals that are greater than or equal to FDI but shorter than TDI, and is reset to zero in response to intervals greater than or equal to TDI and is insensitive to intervals less than FDI. VTEC is compared to a programmed value (VTNID) and VFEC is compared to a corresponding programmable value (VFNID).

Further, when one of the counts equals its corresponding programmable value, the device diagnoses the presence of the corresponding arrhythmia, i.e. fibrillation or tachycardia and delivers an appropriate therapy, e.g. anti-tachycardia pacing, a cardioversion pulse or a defibrillation pulse. In addition, the physician may optionally require that the measured R-R intervals meet a rapid onset criterion before VTEC can be incremented and can also optionally require that should a rate stability criterion fail to be met, VTEC be reset to zero. This detection system has proven effective in distinguishing between fibrillation and ventricular tachycardia so that appropriate therapies may be delivered. However, an increased level of accuracy in classifying rhythms having intervals close to FDI is believed desirable. In addition, the ability to provide a separate therapy set for fast tachycardias as opposed to slower tachycardias is also desirable.

SUMMARY OF THE INVENTION

In a general sense, one aspect of the present invention is to distinguish between a tachycardia occurring in a chamber of a heart (e.g. ventricular tachycardia) from rhythms of a similar average rate, but occurring due to a different cause. Yet another corresponding aspect is to accurately deliver antiarrhythmia therapies to treat the identified tachyarrhythmias.

In one disclosed embodiment, the present invention is employed to accurately distinguish fibrillation from fast tachycardias at similar rates (VT vs. VF, AT vs. AF). In a second disclosed embodiment, the present invention is implemented to distinguish ventricular tachycardia from a rapid ventricular rhythm due to atrial fibrillation (VT vs. AF). In its preferred embodiments, the device takes the form of an implantable pacemaker/cardioverter/defibrillator, and the invention in these embodiments also provides therapies appropriate to the detected tachyarrhythmia. The disclosed embodiments sense the rhythm of the ventricle and provide therapy for the ventricle, but the invention may also be implemented to detect and treat atrial fibrillation and tachycardias.

In accordance with the present invention, it is realized that because of the randomness of sensed intervals between depolarizations during fibrillation or because of uncertainties related to a patient's rhythms, sensed cardiac depolarization intervals during fibrillation may have durations which overlap those observed during tachycardias. From the perspective of a device which diagnoses arrhythmias based on measured intervals or rates, intervals or rates defined as indicative of tachycardia, for example, may in fact be occurring during fibrillation. The present invention in this circumstance provides a method and apparatus for quickly and accurately classifying the nature of a tachyarrhythmia with intervals near the border between the interval or rate ranges associated with tachycardia and fibrillation.

Similarly, ventricular rhythms which may occur due to atrial fibrillation may display an average rate which may overlap with the rates seen during ventricular tachycardia, but generally display substantially more variability of R-R interval duration. The invention provides a method to accurately determine whether the sensed rhythm is a treatable ventricular tachycardia and for avoiding the ineffective delivery of therapies if the rapid rhythm is due to atrial fibrillation.

The disclosed embodiments of the invention operate in the ventricle of the heart and accomplish identification of such rhythms using a methodology which provisionally detects ventricular tachycardia and/or fibrillation and thereafter applies a discrimination function to the series of measured intervals preceding the provisional detection. Discrimination is accomplished by sorting the intervals preceding provisional detection into bins corresponding to interval ranges and examining the relative distribution of the intervals, within the bins. In the relevant embodiments, a predetermined number of intervals are binned, and a determination is made of whether there exists a predetermined number of bins (e.g. two bins), within a designated set of bins, which have a total number of at least a predetermined modesum threshold number of intervals (e.g. 14 intervals), out of a preceding series of a predetermined number of intervals (e.g. 18 intervals). If so, the discrimination criterion is met.

In one embodiment in which the invention is used to distinguish between fast VT and VF, if the discriminator criterion is met, the rhythm is determined to be a fast ventricular tachycardia, and a fast tachycardia therapy (e.g cardioversion or antitachycardia pacing) is delivered. If the discrimination criterion is not met, the rhythm is determined to be fibrillation and a fibrillation therapy (e.g. a defibrillation pulse) is delivered.

Particularly in conjunction with the embodiment of the invention directed toward distinguishing between ventricular tachycardia and ventricular fibrillation, it is desirable that the threshold number of intervals required in order to meet the discrimination criterion should be variable as a function of the underlying rate of the detected rhythm. Specifically, it is desirable that the threshold number should vary as a decreasing function of the cycle lengths of the preceding series of detected depolarizations. In one particular embodiment, for example, the 75th percentile cycle length of the preceding sequence of beats may be employed as a measurement metric, with the threshold number of intervals (expressed as a percentage of intervals binned) decreasing from 100% to 30% in a linear fashion as the 75th percentile cycle length increases. The 75th percentile cycle length of the preceding series of depolarizations may conveniently be calculated by simply selecting the fourth longest interval out of the preceding twelve intervals or by similar methods. In one embodiment, the threshold criteria increases as an inverse function of the length of a defined pecentile interval over a sequence of a predetermined number of intervals separating preceding depolarizations. In one embodiment, the threshold criteria increase as an inverse function of the length of the 75th percentile interval over a sequence of a predetermined number of intervals separating preceding depolarizations.

In one embodiment of the invention (VT vs. VF), it is preferred that the discrimination criterion be applied to discriminate between VT and VF. Specifically, distinguishing between VT and VR is a desirable situation in which the rate or interval based detection criteria for ventricular fibrillation detection are otherwise met, with ventricular tachycardia being detected in the event that the discrimination function is also met.

Further, in one embodiment of the invention relating to VT vs. VF, as the rate of the detected rhythm increases, the required regularity necessary to meet the discrimination criterion increases substantially. This results in the sensitivity of the device to ventricular fibrillation remaining at a high level, while providing a substantial increase in the selectivity of the device to ventricular tachycardia. The resulting benefit is a reduction in unnecessary high voltage shocks in the presence of high rate ventricular tachycardias.

In an embodiment in which the invention is implemented to distinguish between VT and fast ventricular rhythms due to atrial fibrillation (VT vs. AF), if the discriminator criterion is met, the rhythm is determined to be a ventricular tachycardia. Accordingly, a tachycardia therapy (e.g cardioversion or antitachycardia pacing) is delivered. If the criterion is not met, the discrimination criterion is not met, the rhythm is determined to be due to atrial fibrillation and no therapy is delivered.

BRIEF DESCRIPTION OF THE DRAWINGS

The above and still further, features and various aspects of the present invention will become apparent from the following detailed description of a presently preferred embodiment, taken in conjunction with the accompanying drawings, and, in which.

DETAILED DESCRIPTION OF THE PREFERRED EMBODIMENTS

Figure 1:
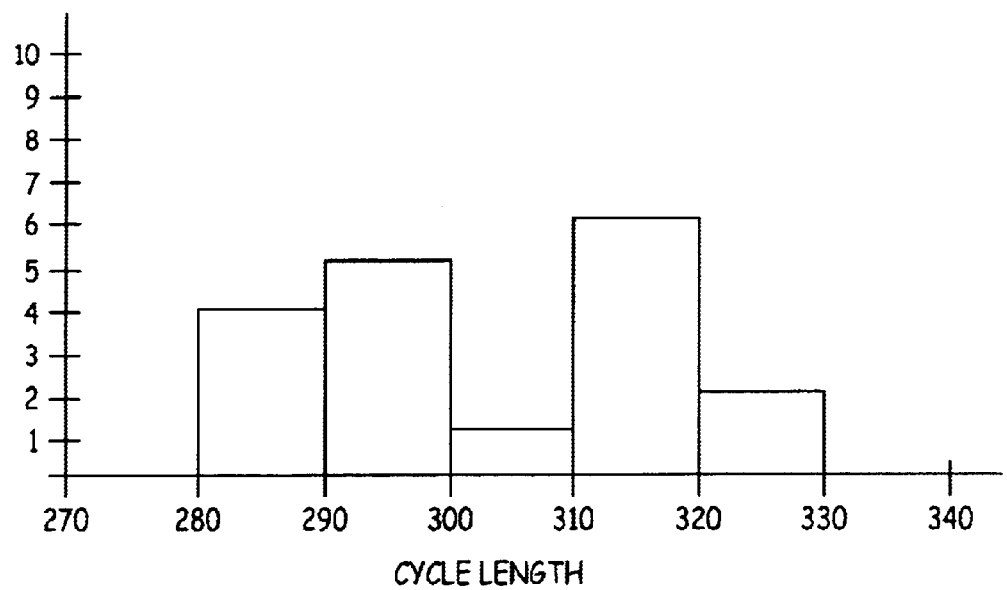
FIG. 1 is an illustration of binned intervals associated with fibrillation.

FIG. 1 illustrates intervals falling within a set of bins, each bin being 10 ms in width. The binned intervals illustrated occurred during an episode of ventricular fibrillation. The 18 intervals preceding initial detection of fibrillation have an average duration of 300–310 milliseconds. An examination of the binned intervals reveals that the two interval bins with the highest values (290–300, 310–320) include 11 total binned intervals.

Figure 2:
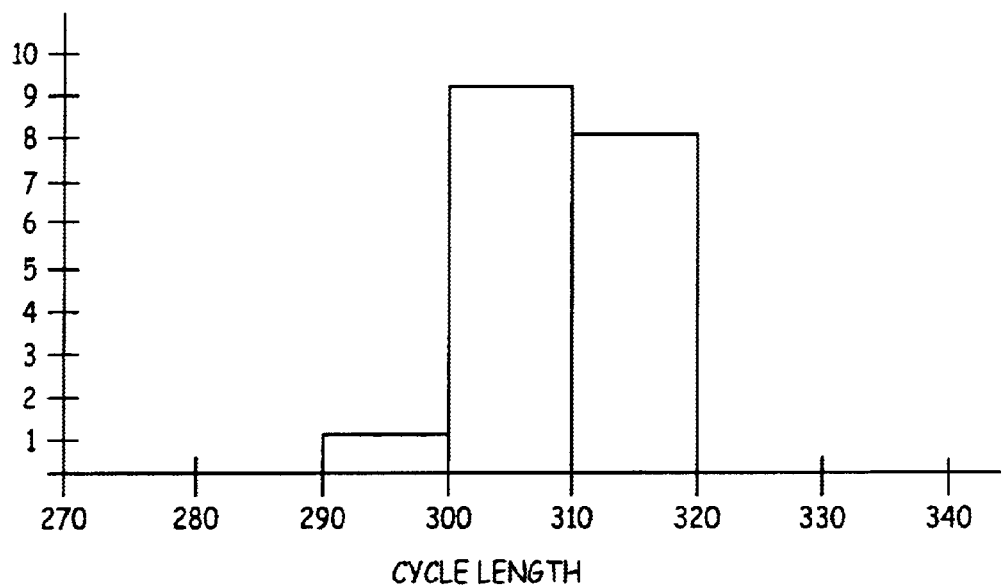
FIG. 2 is an illustration of binned intervals associated with tachycardia.

FIG. 2 illustrates a set of binned intervals obtained during high rate tachycardia, having an average interval length approximately the same as the fibrillation illustrated in FIG. 1. However, 17 out of 18 of the binned intervals fall within two bins. This difference in the distribution of intervals within the bins can be used to distinguish high rate monomorphic ventricular tachycardia from fibrillation, occurring at similar rates. For example, a requirement that 14 out of the 18 binned intervals preceding initial detection of fibrillation fall within two bins within a designated set of bins corresponding to interval ranges greater than a preset value may serve as a mechanism for detecting that the sensed rhythm was ventricular tachycardia, and not fibrillation.

In the context of the first embodiment of the present invention, it is suggested that this discrimination function is applied in response to a provisional detection of ventricular fibrillation. The interval ranges, the numbers of bins, the numbers of intervals and the other parameters of the discriminator function may be programmable by the physician. For example, binned intervals may range from a minimum of 120 to 240 milliseconds to a maximum of 350–400 milliseconds. Alternatively, the value of the maximum interval for tachycardia detection (eg. TDI) may serve as the maximum binned interval.

In the first embodiment disclosed below, the discrimination function is activated in response to detection of a rhythm which could be either ventricular fibrillation or fast ventricular tachycardia. The particular embodiment disclosed accomplishes this provisional detection function, using a modified version of the detection methodology implemented in the Medtronic implantable pacemaker/cardioverter/defibrillators. However, the present invention may be implemented in any device capable of detecting an arrhythmia which is not unambiguously identified as either tachycardia or fibrillation. Thus, the present invention is adaptable to devices having basic detection methodologies similar to any of those disclosed in the prior art.

Figure 3:
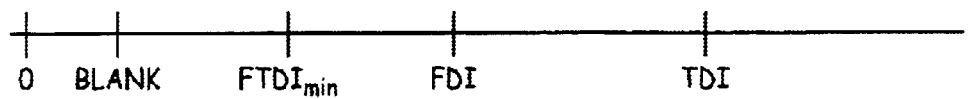
FIG. 3 is an illustration of the defined intervals employed in the first preferred embodiment of the present invention.

FIG. 3 is an illustration of the rate ranges which are employed in the first preferred embodiment of the present invention. The range of intervals which are taken as indicative of sinus rhythm include those which are greater than or equal to TDI. The range of intervals taken as indicative of tachycardia include intervals less than TDI, but greater than or equal to FDI. The range of intervals taken as indicative of fibrillation include intervals less than FDI and greater than or equal to the blanking interval. If ventricular fibrillation is provisionally detected, bins corresponding to intervals greater than or equal to $FDTI_{min}$ are examined and are employed in the discrimination function.

In the first embodiment of the invention discussed below, using interval ranges corresponding to FIG. 3, the tachycardia and fibrillation detection criteria discussed above in conjunction with the Medtronic implantable pacemaker/cardioverter/defibrillators are retained, and used as one set of criteria for provisional detection of tachycardia or fibrillation. In addition to the fibrillation and tachycardia detection criteria discussed above, (i.e. VFEC=VFNID or VTEC=VTNID), provisional detection of tachycardia or fibrillation detection may also or alternatively be accomplished using a combined count of all intervals indicative of tachycardia or fibrillation. This combined count (VFEC+VTEC) is compared to a combined count threshold (CNID). If VTEC+VFEC is equal or greater than CNID, the device checks to see whether VFEC is at least a predetermined number (e.g. 6). If so, the device checks to determine how many of a number (e.g. 8) of the immediately preceding intervals are greater or equal to FDI. If a predetermined number (e.g. 8) are greater than or equal to FDI, tachycardia is provisionally detected, otherwise ventricular fibrillation is provisionally detected. The immediately preceding measured intervals are then examined as discussed below to determine whether the provisional detection of fibrillation should be confirmed or amended to indicate detection of fast ventricular tachycardia.

Figure 6:
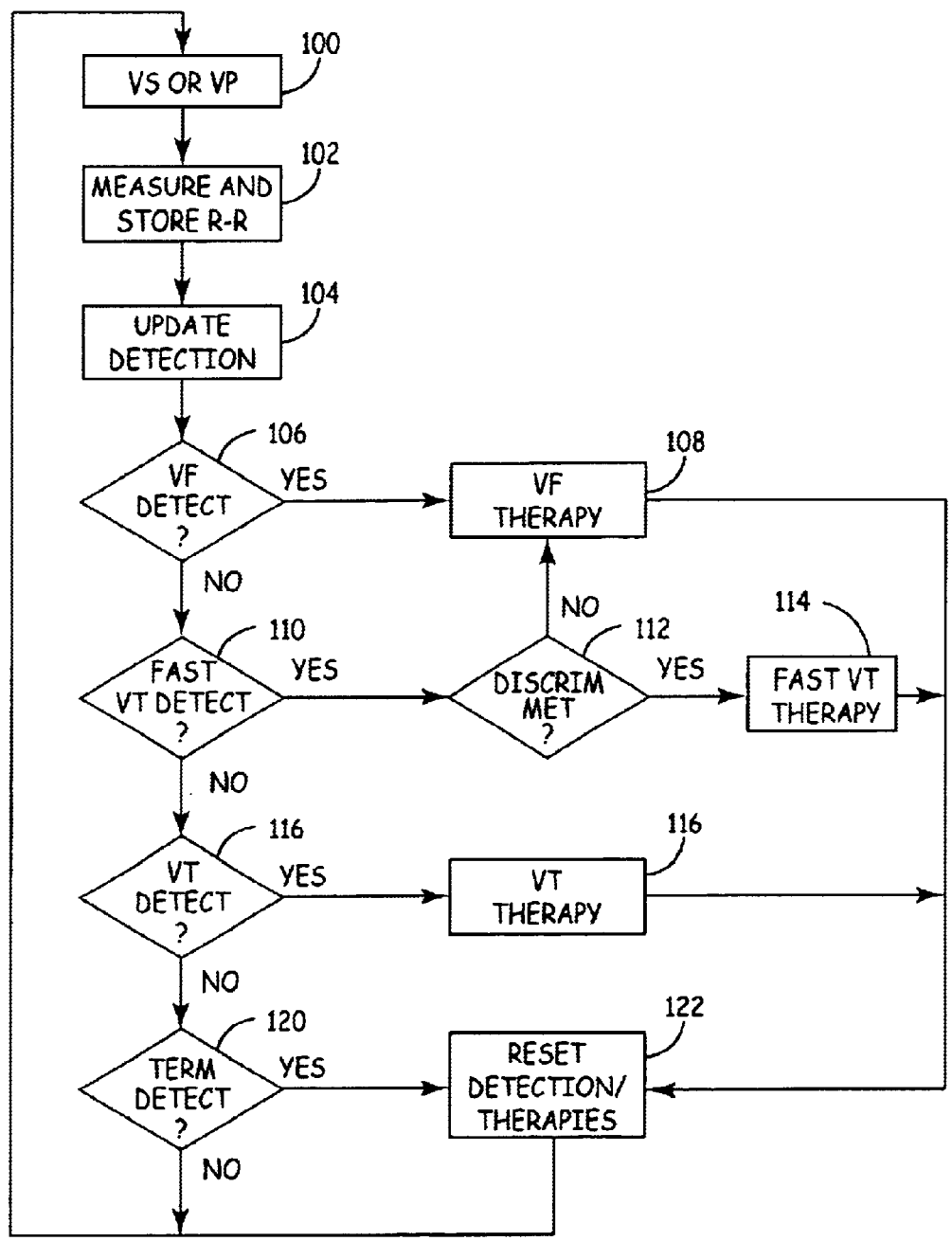
FIG. 6 is a simplified flow chart diagram illustrating the functional operation of a second preferred embodiment of the present invention.

The present invention, in the first preferred embodiment, is practiced by adding specific new features to the underlying detection methodology of existing prior devices. However, the present invention is not limited to the context of the specific detection criteria disclosed, but is applicable to any devices which distinguish between tachycardia and fibrillation using rate or interval based criteria. For example, FIG. 6 illustrates an alternative method of employing the present invention to distinguish between VF and fast VT.

Figure 4:
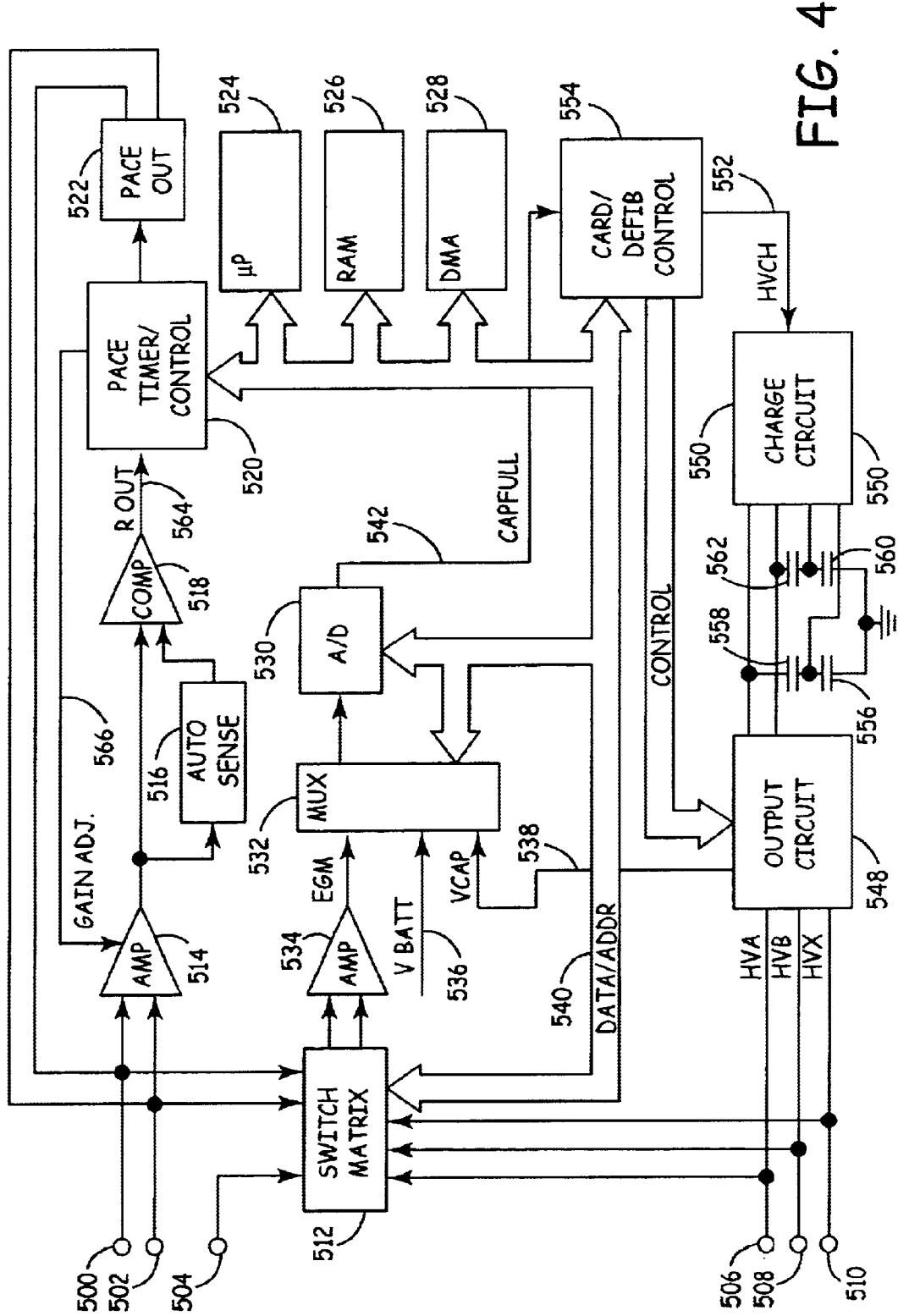
FIG. 4 is a simplified block diagram illustrating the components of a device within which the method and apparatus of the present invention may be implemented.

FIG. 4 is a functional schematic diagram of an implantable pacemaker/cardioverter/defibrillator in which the present invention may be practiced. This diagram should be taken as exemplary of the type of device in which the invention may be embodied, and not as limiting, as it is believed that the invention may usefully be practiced in a wide variety of device implementations, including devices having functional and structured organization similar to any of the implantable pacemaker/defibrillator/cardioverters and similar devices. The invention is also believed practicable in conjunction with implantable pacemaker/cardioverters/defibrillators as disclosed in prior U.S. Pat. No. 4,548,209, issued to Wielders, et al. on Oct. 22, 1985, U.S. Pat. No. 4,693,253, issued to Adams et al. on Sep. 15, 1987, U.S. Pat. No. 4,830,006, issued to Haluska et al. on May 6, 1989 and U.S. Pat. No. 4,949,730, issued to Pless et al. on Aug. 21, 1990, all of which are incorporated herein by reference in their entireties.

The device is illustrated as being provided with six electrodes, 500, 502, 504, 506, 508 and 510. Electrodes 500 and 502 may be a pair of endocardial electrodes located in the ventricle, mounted to a transvenous lead. Electrode 504 may correspond to a remote, indifferent electrode located on the housing of the implantable pacemaker/cardioverter/defibrillator. Electrodes 506, 508 and 510 may correspond to the large surface area defibrillation electrodes located on ventricular, coronary sinus, superior vena cava or subcutaneous leads, to electrodes located on or part of the device housing or to epicardial defibrillation electrodes.

Electrodes 500 and 502 are shown as hard-wired to the R-wave detector circuit, comprising band-pass filter circuit 514, auto threshold circuit 516 for providing an adjustable sensing threshold as a function of the measured R-wave amplitude and comparator 518. A signal is generated on R-out line 564 whenever the signal sensed between electrodes 500 and 502 exceeds the present sensing threshold defined by the auto threshold circuit 516. As illustrated, the gain on the band pass amplifier 514 is also adjustable by means of a signal from the pacer timing and control circuitry 520 on GAIN ADJ line 566.

The operation of this R-wave detection circuitry may correspond to that disclosed in commonly assigned U.S. Pat. No. 5,118,824, issued to Keimel and incorporated herein by reference in its entirety. However, alternative R-wave detection circuitry such as that illustrated in U.S. Pat. No. 4,819,643, issued to Menken on Apr. 11, 1989 and U.S. Pat. No. 4,880,004, issued to Baker et al. on Nov. 14, 1989, both incorporated herein by reference in their entireties, may also usefully be employed to practice the present invention.

The threshold adjustment circuit 516 sets a threshold corresponding to a predetermined percentage of the amplitude of a sensed R-wave, which threshold decays to a minimum threshold level over a period of less than three seconds thereafter, similar to the automatic sensing threshold circuitry illustrated in the article "Reliable R-Wave Detection from Ambulatory Subjects", by Thakor et al., published in Biomedical Science Instrumentation, Vol. 4, pp. 67–72, 1978, incorporated herein by reference in its entirety. The invention may also be practiced in conjunction with more traditional R-wave sensors of the type comprising a band pass amplifier and a comparator circuit to determine when the band-passed signal exceeds a predetermined, fixed sensing threshold.

Switch matrix 512 is used to select which of the available electrodes are coupled to band pass amplifier 534. Selection of which two electrodes are so coupled is controlled by the microprocessor 524 via data/address bus 540. Signals from the selected electrodes are passed through band-pass amplifier 534 and into multiplexer 532, where they are converted to multi-bit digital signals by A/D converter 530, for storage in random access memory 526 under control of direct memory address circuit 528. Microprocessor 524 analyzes the digitized EGM signal stored in random access memory 526 to determine the width of the stored R-wave or in conjunction with the tachycardia/fibrillation discrimination function discussed below.

Amplifier 534 may be a broad band pass amplifier, having a band pass extending for approximately 0.5 to 200 hertz. The filtered EGM signal from amplifier 534 is passed through multiplexer 532, and digitized in A-D converter circuitry 530. The digitized EGM data is stored in random access memory 526 under control of direct memory address circuitry 528. Preferably, a portion of random access memory 526 is configured as a looping or buffer memory which stores at least the preceding several seconds of the EGM signal.

The occurrence of an R-wave detection signal on line 564 is communicated to microprocessor 524 via data/address bus 540, and microprocessor 524 notes the time of its occurrence, calculates the R-R interval and stores it for later reference. The stored R-R intervals may be stored in a buffer memory so that only the most recent series of intervals are stored, in the same fashion as the ECG. The microprocessor also updates counts related to the R-R intervals previously sensed. The counts, VFEC and VTEC, are incremented on the occurrence of a measured R-R intervals falling within the fibrillation and ventricular tachycardia ranges, respectively, as discussed above. These rate ranges may be defined by the programming stored in the RAM 526.

These counts, along with other stored information reflective of the previous series of R-R intervals such as information regarding the rapidity of onset of the detected short R-R intervals, the stability of the detected R-R intervals, the duration of continued detection of short R-R intervals, the average R-R interval duration and information derived from analysis of stored EGM segments are used to determine whether tachyarrhythmias are present and to distinguish between different types of tachyarrhythmias, as discussed above in conjunction with FIG. 3. Other such detection algorithms for recognizing tachycardias are described in the above cited U.S. Pat. No. 4,726,380, issued to Vollmann, U.S. Pat. No. 4,880,005, issued to Pless et al. and U.S. Pat. No. 4,830,006, issued to Haluska et al., incorporated by reference in their entireties herein. An additional set of tachycardia recognition methodologies is disclosed in the article "Onset and Stability for Ventricular Tachyarrhythmia Detection in an Implantable Pacer-Cardioverter-Defibrillator" by Olson et al., published in *Computers in Cardiology*, Oct. 7–10, 1986, IEEE Computer Society Press, pages 167–170, also incorporated by reference in its entirety herein. However, other criteria may also be measured and employed in conjunction with the present invention.

It is envisioned that onset and stability requirement are optional in a device employing the present invention, and preferably are made available as programmable options, which may be deleted by external programmer command. If included, it is believed preferable that the onset criteria be required to be met prior to initiating counting of VTEC, and that once met, the criterion will remain satisfied until detection of tachycardia termination. Thus, onset is not intended to be a detection criteria required for re-detection of tachycardia, following initial detection. The width criterion, if used, should also be understood to preferably be used only in initial detection of tachycardia. This reflects a presumption that following initial detection of ventricular tachycardia, absent a proven return to normal heart rhythm (termination detect), subsequent high ventricular rates should be presumed to be ventricular in origin. The stability criterion, on the other hand, is believed to be appropriate for use both in initial detection of tachycardia and in re-detection of tachycardia.

The remainder of the circuitry is dedicated to the provision of cardiac pacing, cardioversion and defibrillation therapies. The pacer timing/control circuitry 520 includes programmable digital counters which control the basic time intervals associated with VVI mode cardiac pacing, including the pacing escape intervals, the refractory periods during which sensed R-waves are ineffective to restart timing of the escape intervals and the pulse width of the pacing pulses. The durations of these intervals are determined by microprocessor 524, and are communicated to the pacing circuitry 520 via address/data bus 540. Pacer timing/control circuitry also determines the amplitude of the cardiac pacing pulses and the gain of band-pass amplifier, under control of microprocessor 524.

During VVI mode pacing, the escape interval counter within pacer timing/control circuitry 520 is reset upon sensing of an R-wave as indicated by a signal on line 564, and on timeout triggers generation of a pacing pulse by pacer output circuitry 522, which is coupled to electrodes 500 and 502. The escape interval counter is also reset on generation of a pacing pulse, and thereby controls the basic timing of cardiac pacing functions, including anti-tachycardia pacing. The duration of the interval defined by the escape interval timer is determined by microprocessor 524, via data/address bus 540. The value of the count present in the escape interval counter when reset by sensed R-waves may be used to measure the duration of R-R intervals, to detect the presence of tachycardia and to determine whether the minimum rate criteria are met for activation of the width measurement function.

Microprocessor 524 operates as an interrupt driven device, and responds to interrupts from pacer timing/control circuitry 520 corresponding to the occurrence of sensed R-waves and corresponding to the generation of cardiac pacing pulses. These interrupts are provided via data/address bus 540. Any necessary mathematical calculations to be performed by microprocessor 524 and any updating of the values or intervals controlled by pacer timing/control circuitry 520 take place following such interrupts.

In the event that a tachyarrhythmia is detected, and an antitachyarrhythmia pacing regimen is desired, appropriate timing intervals for controlling generation of anti-tachycardia pacing therapies are loaded from microprocessor 524 into the pacer timing and control circuitry 520, to control the operation of the escape interval counter and to define refractory periods during which detection of an R-wave by the R-wave detection circuitry is ineffective to restart the escape interval counter. Similarly, in the event that generation of a cardioversion or defibrillation pulse is required, microprocessor 524 employs the counters in timing and control circuitry 520 to control timing of such cardioversion and defibrillation pulses, as well as timing of associated refractory periods during which sensed R-waves are ineffective to reset the timing circuitry.

In response to the detection of fibrillation or a tachycardia requiring a cardioversion pulse, microprocessor 524 activates cardioversion/defibrillation control circuitry 554, which initiates charging of the high voltage capacitors 556, 558, 560 and 562 via charging circuit 550, under control of high voltage charging line 552. The voltage on the high voltage capacitors is monitored via VCAP line 538, which is passed through multiplexer 532, and, in response to reaching a predetermined value set by microprocessor 524, results in generation of a logic signal on CAP FULL line 542, terminating charging. Thereafter, delivery of the timing of the defibrillation or cardioversion pulse is controlled by pacer timing/control circuitry 520. One embodiment of an appropriate system for delivery and synchronization of cardioversion and defibrillation pulses, and controlling the timing functions related to them is disclosed in more detail in allowed, commonly assigned U.S. Pat. No. 5,188,105, issued Feb. 23, 1993 to Keimel, for an Apparatus for Detecting and Treating a Tachyarrhythmia, incorporated herein by reference in its entirety. However, any known cardioversion or defibrillation pulse generation circuitry is believed usable in conjunction with the present invention. For example, circuitry controlling the timing and generation of cardioversion and defibrillation pulses as disclosed in U.S. Pat. No. 4,384,585, issued to Zipes on May 24,1983, in U.S. Pat. No. 4,949,719 issued to Pless et al., cited above, and in U.S. Pat. No. 4,375,817, issued to Engle et al., all incorporated herein by reference in their entireties may also be employed. Similarly, known circuitry for controlling the timing and generation of anti-tachycardia pacing pulses as described in U.S. Pat. No. 4,577,633, issued to Berkovits et al. on Mar. 25, 1986, U.S. Pat. No. 4,880,005, issued to Pless et al. on Nov. 14, 1989, U.S. Pat. No. 7,726,380, issued to Vollmann et al. on Feb. 23, 1988 and U.S. Pat. No. 4,587,970, issued to Holley et al. on May 13, 1986, all of which are incorporated herein by reference in their entireties may also be used.

In modern pacemaker/cardioverter/defibrillators, the particular anti-tachycardia and defibrillation therapies are programmed into the device ahead of time by the physician, and a menu of therapies is typically provided. For example, on initial detection of tachycardia, an anti-tachycardia pacing therapy may be selected. On re-detection of tachycardia, a more aggressive anti-tachycardia pacing therapy may be scheduled. If repeated attempts at anti-tachycardia pacing therapies fail, a higher level cardioversion pulse therapy may be selected thereafter. Prior art patents illustrating such pre-set therapy menus of antitachyarrhythmia therapies include the above-cited U.S. Pat. No. 4,830,006, issued to Haluska, et al., U.S. Pat. No. 4,727,380, issued to Vollmann et al. and U.S. Pat. No. 4,587,970, issued to Holley et al. The present invention is believed practicable in conjunction with any of the known anti-tachycardia pacing and cardioversion therapies, and the present invention may be practiced in conjunction with a device in which the choice and order of delivered therapies is programmable by the physician, as in current implantable pacemaker/cardioverter/defibrillators or similar devices.

In addition to varying the therapy delivered following a failed attempt to terminate a tachyarrhythmia, it is also known that adjustment of detection criteria may be appropriate. For example, adjustment may comprise reducing the number of intervals required to detect a tachyarrhythmia to allow a more rapid re-detection or by changing the interval ranges to bias detection towards detection of ventricular fibrillation, for example as disclosed in U.S. Pat. No. 4,971,058, issued to Pless et al and incorporated herein by reference in its entirety.

In the present invention, selection of the particular electrode configuration for delivery of the cardioversion or defibrillation pulses is controlled via output circuit 548, under control of cardioversion/defibrillation control circuitry 554 via control bus 546. Output circuit 548 determines which of the high voltage electrodes 506, 508 and 510 will be employed in delivering the defibrillation or cardioversion pulse regimen, and may also be used to specify a multi-electrode, simultaneous pulse regimen or a multi-electrode sequential pulse regimen. Monophasic or biphasic pulses may be generated. One example of circuitry which may be used to perform this function is set forth in U.S. Pat. No. 5,163,427, issued to Keimel, incorporated herein by reference in its entirety. However, output control circuitry as disclosed in U.S. Pat. No. 4,953,551, issued to Mehra et al. on Sep. 4, 1990 or U.S. Pat. No. 4,800,883, issued to Winstrom on Jan. 31, 1989 both incorporated herein by reference in their entireties, may also be used in the context of the present invention. Alternatively single monophasic pulse regimens employing only a single electrode pair according to any of the above cited references which disclose implantable cardioverters or defibrillators may also be used.

Figure 5A:
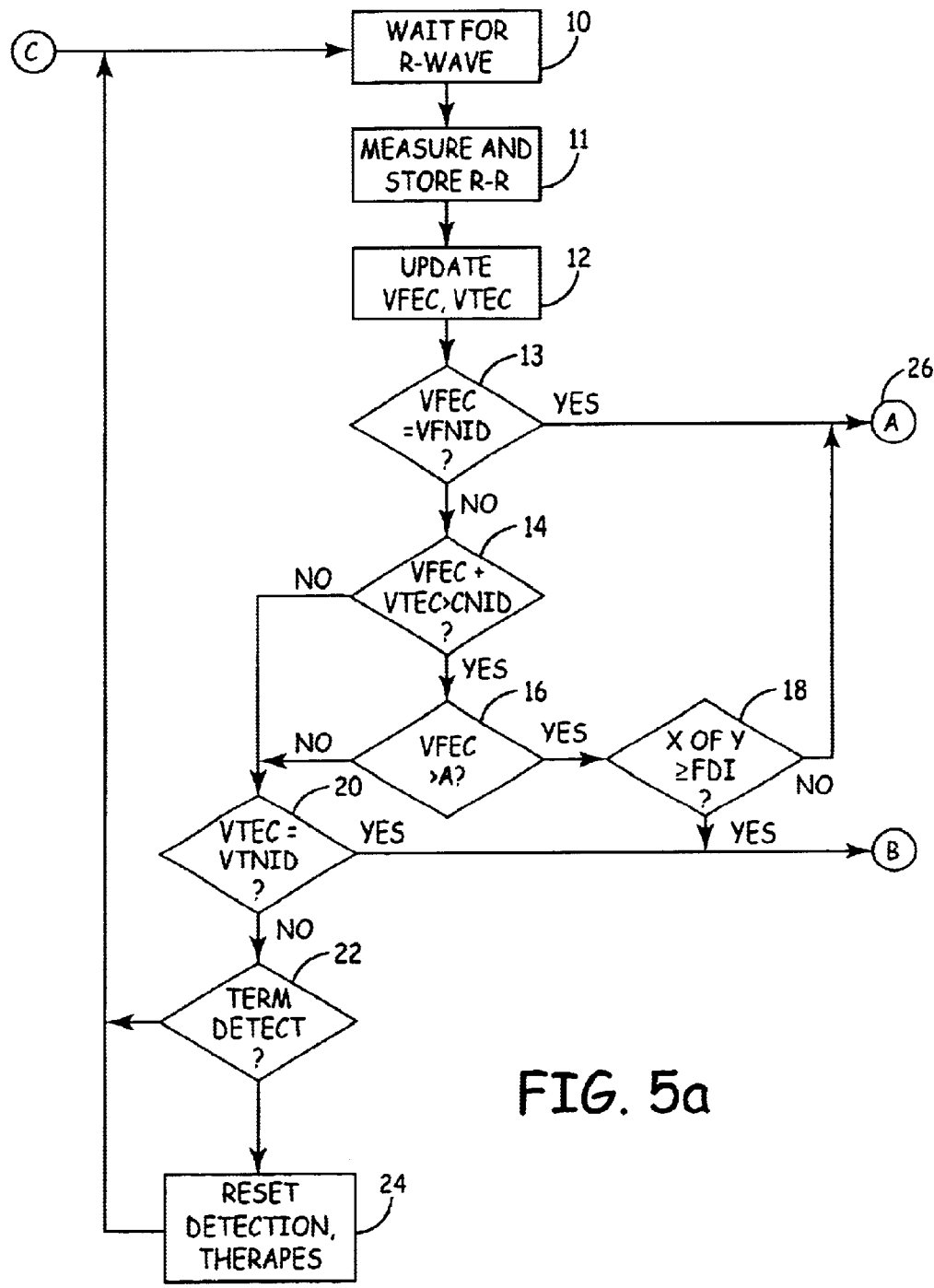
FIGS. 5a, 5b and 5c are simplified flow chart diagrams illustrating the functional operation of a first preferred embodiment of the present invention.
Figure 5B:
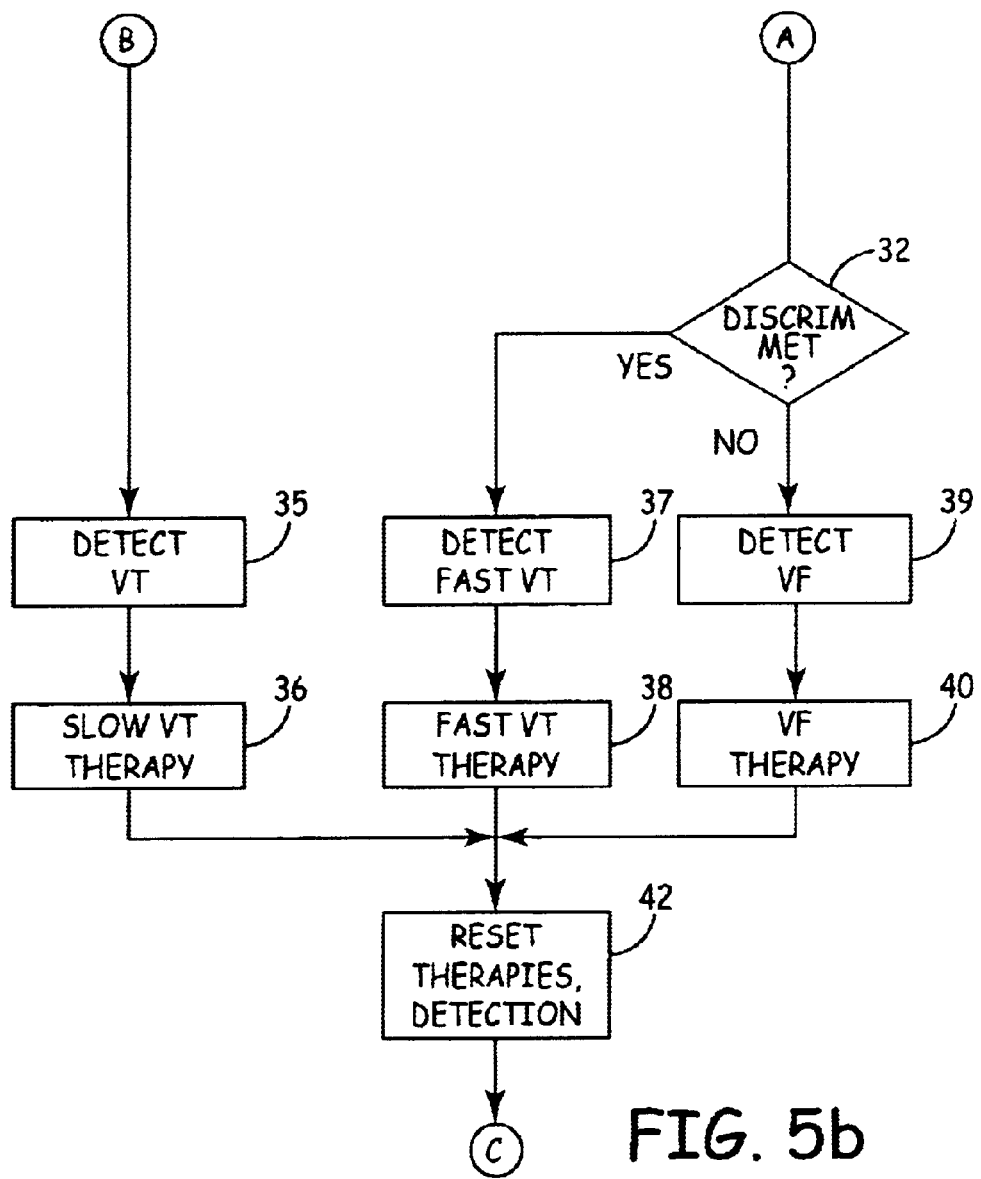
Figure 5C:
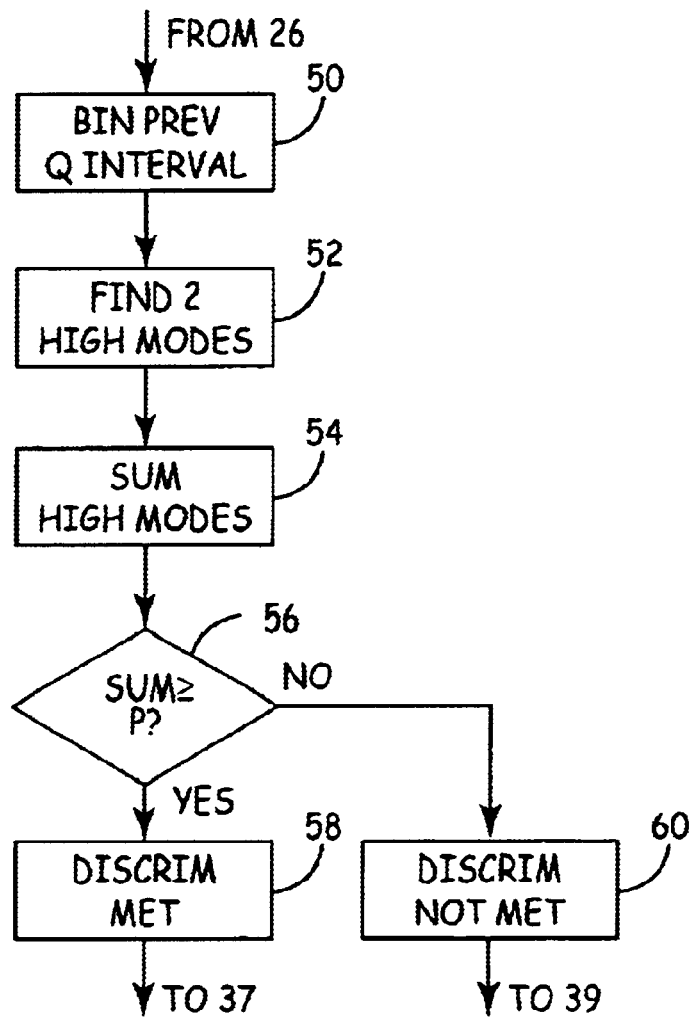

FIGS. 5a, 5b and 5c are functional flow charts illustrating the operation of the first preferred embodiment of the present invention, as embodied in the context of a device illustrated in FIG. 2. In FIG. 5a, it should be understood that the device may be in general operating as a demand pacemaker, and that the analysis undertaken takes place in response to the occurrence of sensed or paced depolarizations of the heart. At 10, the device is a awaiting the occurrence of the next subsequent R-wave. Uppon occurrenceof the R-wave, the processes and functions described above related to storing the time of occurrence of the R-wave, measuring and storing the R-R interval preceding the R-wave are performed at 11. At 12, VTEC and VFEC counts are updated.

At 13, device checks to determine whether VFEC equals VFNID. If so, fibrillation is provisionally detected. If not, the sum of VFEC and VTEC is compared to CNID at 14. If their sum is equal to or greater than CNID, the device checks at 16 to determine whether VFEC is greater than a predetermined number, for example 5. If so, the device checks at 18 to see whether a predetermined number X of the preceding Y R-R intervals (e.g. at least 7 or all 8 out of the preceding 8 intervals) are greater than or equal to FDI. If so tachycardia is provisionally detected, if not, fibrillation is provisionally detected.

In the event that either the sum of VFEC+VTEC is less than CDIN at 14 or VFEC is less than or equal to A at 16, the device checks at 20 to determine whether VTEC equals VTNID. If so, ventricular tachycardia is detected if not, the device checks at 22 to determine whether a tachyarrhythmia has previously been detected and whether the previous series of R-waves indicate termination of the previously detected tachyarrhythmia. Detection of termination of tachycardia or fibrillation may be accomplished by means of detection of a predetermined number (e.g. 8) of sequential R-R intervals indicative of normal heart rate. Normal heart rate may be defined as R-R intervals greater than or equal to TDI. If termination is detected, detention criteria and anti-arrhythmia therapy menus are reset at 24, as described above in conjunction whit FIG. 4. If not, the device simply waits for the next R-wave at 10.

In the event that tachycardia is provisionally detected at 18 or 20, the device simply proceeds to detect slow VT at 35 (FIG. 5b) and to deliver slow VT therapy at 36. In the event that fibrillation is provisionally detected at 13 or 18, the device checks at 32 (FIG. 5b) to determine whether the discrimination criterion is met. If the criterion is not met, ventricular fibrillation is detected at 39 and fibrillation therapy is deliberated at 40. If the criterion is met, fast ventricular tachycardia is detected at 37 and fast VT therapy is delivered at 38. After delivery of therapy at 36, 38 or 40 or following inhibition of anti-tachycardia therapy at 34, the therapy menus and detection criteria are reset at 42 to reflect the preceding detection of tachyarrhythmia and delivery of tachyarrhythmia therapy, as discussed above in conjunction with FIG. 4. The device them returns to block 10, awaiting the next successive R-wave, so that it may determine whether the tachyarrhythmia has been terminated, persists, or has changed to another type of tachyarrhythmia.

FIG. 5c illustrates the discrimination function in more detail, and corresponds to block 32 of FIG. 5b. At 50, the microprocessor reads the most recent 18 stored intervals and sorts them into corresponding interval ranges or bins as illustrated in FIGS. 1 and 2. For purposes of the present embodiment, interval ranges or bins 10 ms in width are believed workable, although other bin widths may be employed. Intervals greater than a programmable short interval threshold, e.g. 120 or 240 ms are excluded from the bins. At 52, the microprocessor determines which two bins hold the greatest numbers of interval and at 54 the numbers of intervals in the two identified bins are summed. At 56, an elevation is made to determine whether the sum greater than or equal to the defined threshold number "P" of intervals. If the sum is greater or equal to "P", then discrimination criterion is considered to be met at 58 and the logic proceeds to 37. If not, the criterion is considered unfulfilled at 60 and the logic proceeds to 39. The value of "P" may be fixed, for example at 14 or may vary according to a more preferred embodiment of the present invention.

Particularly in the context of a device as described in conjunction with FIGS. 5a through 5c, in which the discrimination function is intended to distinguish between ventricular fibrillation and ventricular tachycardia, and more particularly in those situations in which the discrimination function is entered in response to a provisional diagnosis of ventricular fibrillation, it is desirable that the value of the defined threshold "P" vary as a function of the cycle lengths of the preceding series of depolarizations.

Figure 8A:
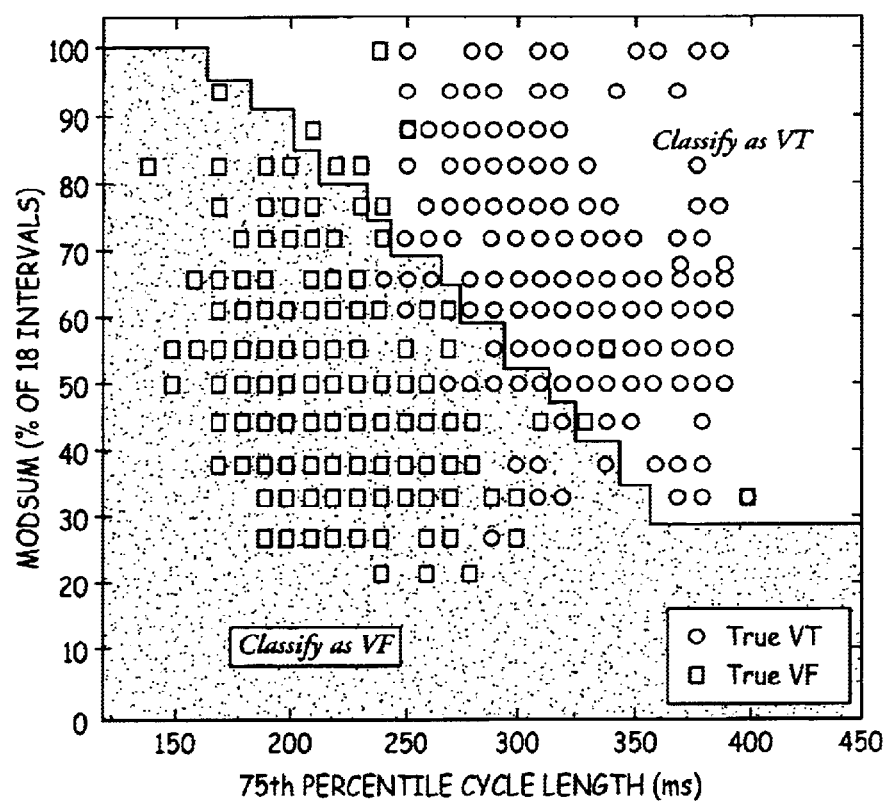
FIGS. 8a–c are charts illustrating operation of a preferred embodiment of the present invention employed to distinguish ventricular fibrillation from ventricular tachycardia.
Figure 8B:
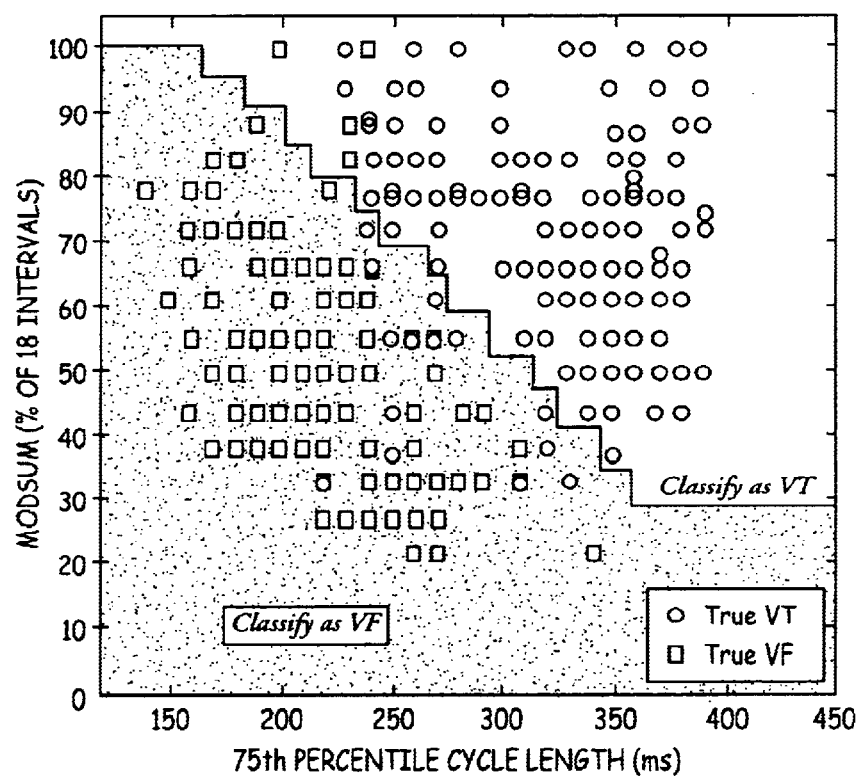
Figure 8C:
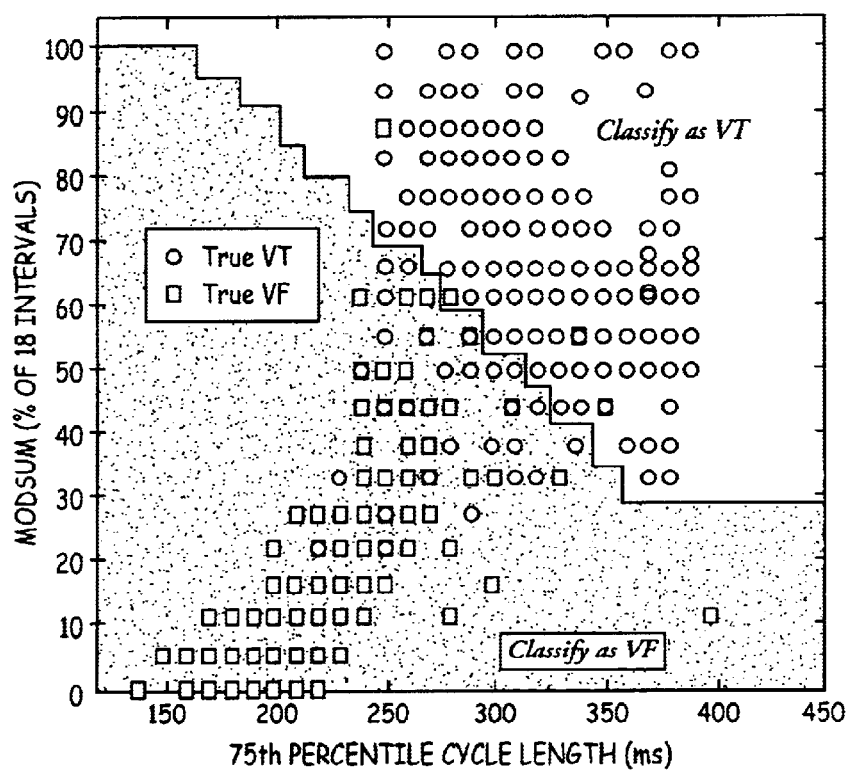

In the scatter plots of FIGS. 8a–c, the discrimination criterion is applied to recorded electrograms which have been classified as ventricular fibrillation or ventricular tachycardia by a panel of experts to determine the sensitivity and selectivity of the discrimination criterion. The classification of the electrograms by the expert panel is illustrated by the shape (square or round) of the illustrated data point for each electrogram, and the electrogram data points are located on the charts as a function of their modesums (sums of the two bins containing the most intervals) and their 75th percentile cycle lengths.

FIG. 8a is a scatter plot illustrating operation of a device in which the value of "P" (expressed as a percentage of the preceding 18 binned intervals) decreases linearly as an inverse function of the 75th percentile cycle length of the preceding intervals. In this case, the microprocessor identifies the 75th percentile of cycle length by simply selecting the fourth longest interval of the preceding twelve R-R intervals. As illustrated in FIG. 8a, as the 75th percentile cycle length decreases from 150 milliseconds to approximately 350 milliseconds, the threshold "P", expressed as a percentage of the preceding 18 intervals decreases from 100% to 30%. In the scatter plot illustrated in FIG. 8a, the minimum interval which is available for binning is 120 milliseconds.

FIGS. 8b and 8c are additional scatter plots illustrating the operation of the discriminator in conjunction with minimum short intervals available for binning of 120 milliseconds (FIG. 8b) and 240 milliseconds (FIG. 8c). In all three charts, it can be seen that the discriminator criterion employing a value of "P" which varies according to the illustrated function provides highly accurate discrimination between ventricular tachycardia and ventricular fibrillation, while retaining a high sensitivity to ventricular fibrillation. In interpreting the flow chart of FIG. 5c, for devices employing a variable value of the threshold "P" number of intervals required to be present in the two highest valued bins, it should be understood that the microprocessor calculates the value of "P" following each sensed R-wave, as a linearly decreasing function of the value of the 75th percentile cycle length of the preceding sequence of twelve R-R intervals.

While the parameters described above are believed workable with most patients, other parameters may be employed. For example, if bins having widths of less than 10 ms are employed, the threshold number may be compared to the summed counts in three or more bins. Similarly, the number of preceding intervals binned and the threshold number of intervals may also be varied, as can the values of FDI, $FDTI_{min}$ and FDI.

FIG. 6 is a functional flow chart illustrating a more general application of the present invention in the context of an implantable pacemaker/cardioverter/defibrillator, of the type generally illustrated and described in conjunction with FIG. 4, but not employing the specific methodologies for provisional detection of arrhythmias set forth above. At 100, the device awaits the occurrence of a ventricular depolarization, sensed or paced. At 102, the device measures and stores the preceding R-R interval and at 104, updates its detection methodology. For purposes of FIG. 6, it should be understood that the device may employ an interval based detection methodology as described above, or may employ a rate-based detection methodology, depending upon the average rate, or depending upon a mixture of average rate and intervals, as disclosed in the Pless et al. U.S. Pat. No. 4,969,465, cited above. At 104 the device checks to see whether criteria for provisional detection of ventricular fibrillation are met. If so, a defibrillation pulse is generated at 108, the detection and therapy menus are reset at 122 and the device returns to bradycardia pacing, awaiting the next paced or sensed ventricular event.

In the event that ventricular fibrillation is not unambiguously identified at 106, the device checks at 110 to determine whether a rhythm which could be either a fast ventricular tachycardia or fibrillation has occurred. In the context of devices employing multiple rate ranges, with corresponding detection criteria for each rate range, this may correspond to the provisional detection of fast ventricular tachycardia. Alternatively, this could correspond to a detection of a rhythm that overlaps rate or interval boundaries associated with provisional detection of fibrillation and ventricular tachycardia, in a system employing essentially two interval ranges. Regardless of the specific detection methodology employed, identification of a rhythm which has a rate and/or average interval consistent with either VF or VT activates the discriminator function at 112. The discriminator function corresponds to FIG. 5c, illustrated above. In the event that the discriminator criteria is not met, defibrillation is administered at 108, in substantially the same manner as described in conjunction with FIG. 5b above. In the event that the discrimination criteria is met, a fast ventricular tachycardia therapy is delivered at 114, and the detection and therapy menus are updated at 122.

If the device does not detect a rhythm at 110, which could be indicative of either tachycardia or fibrillation, it checks at 116 to decide whether a rhythm which is identifiable as a slower ventricular tachycardia has been detected. If so, antitachycardia therapy is delivered at 118 and the detection and therapy menus are reset at 122. If not, the device checks at 120 to determine whether determination of any previously detected tachycardias or fibrillation has been detected. If so, the detection and therapy menus are reset at 122, if not, the device continues to function as a VVI pacemaker, awaiting the next sensed or paced ventricular depolarization at 100.

Figure 7:
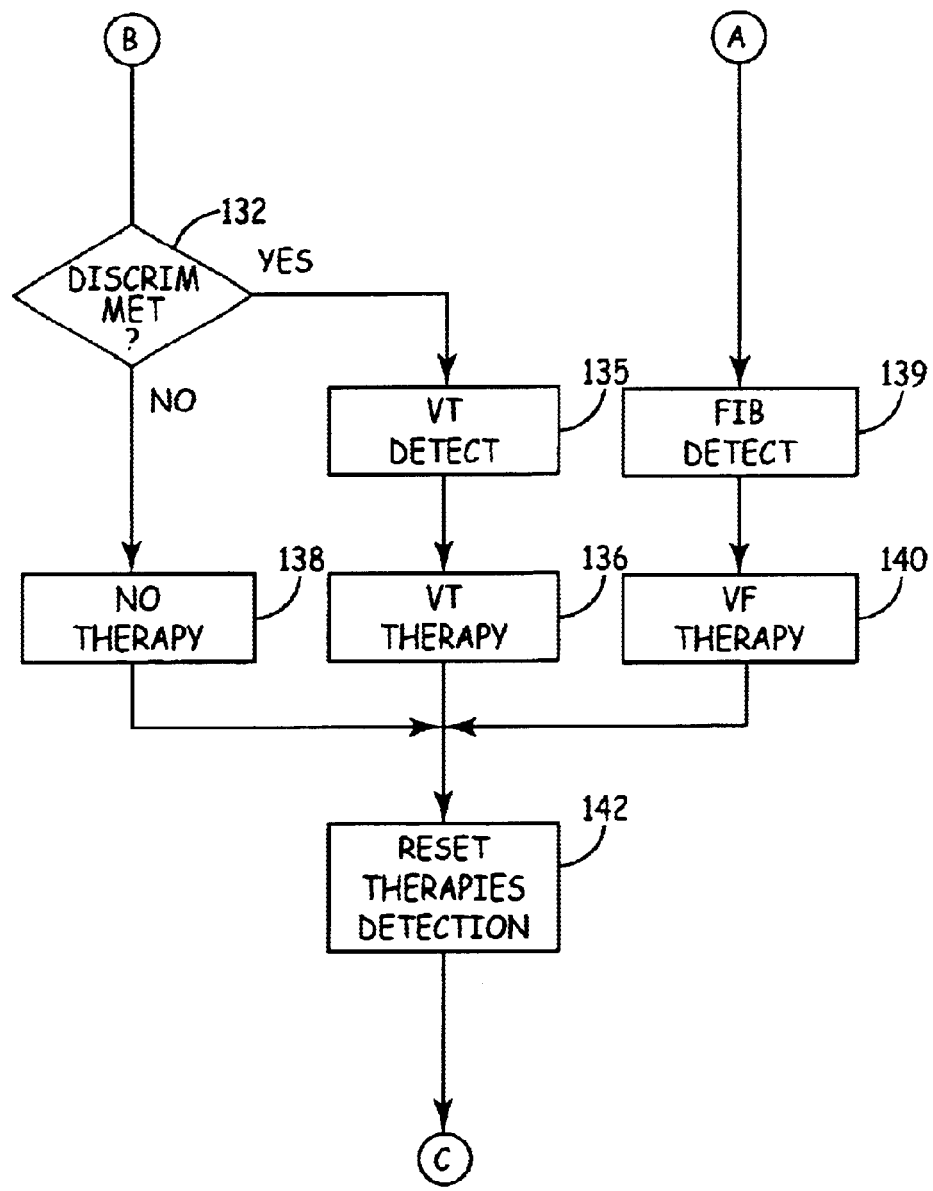
FIG. 7 is a simplified flow chart diagram illustrating the functional operation of a third preferred embodiment of the present invention.

FIG. 7 illustrates a third embodiment of the present invention in which the discrimination function is used to distinguish between VT and rapid ventricular rhythms due to atrial fibrillation. In this embodiment, provisional detection of VT activates the discriminator function. If the discriminator criterion is not met, the rhythm is presumed to be due to atrial fibrillation and no therapy is delivered. This embodiment should be understood to be practiced in a device otherwise as described in conjunction with FIGS. 4, 5*a* and 5*c*. FIG. 7 may be directly substituted for FIG. 5*b*, and the discriminator function corresponds to that illustrated in FIG. 5*c*.

In the event that tachycardia is detected at 18 or 20, the device checks at 132 to decide whether discrimination criterion is met. If the criterion is not met, therapy is aborted at 138. If the criterion is met, ventricular tachycardia is detected at 135 and VT therapy is delivered at 136. In the event that fibrillation is provisionally detected at 13 or 18, the device detects the occurrence of fibrillation at 139 and delivers a defibrillation pulse at 140. After delivery of therapy at 136 or 140 or following cancellation of therapy at 138 the therapy menus and detection criteria are reset at 142 to reflect the preceding detection of tachyarrhythmia and delivery of or cancellation of tachyarrhythmia therapy, as discussed above in conjunction with FIG. 4. The device then returns to block 10, (FIG. 5*a*), awaiting the next successive R-wave, so that it may determine whether the detected tachyarrhythmia has been terminated, persists, or has changed to another type of tachyarrhythmia.

Referring to FIG. 7, the discriminator function at 132 corresponds to that illustrated in FIG. 5*c*. However, the number of intervals binned, the number of bins available to meet the threshold value and the threshold value may vary from those used when the discriminator is activated in response to a provisional detection of VF. In such a case, it is anticipated that the physician may wish to optimize the discrimination function parameters based on a physiologic work-up of the individual patient. While FIGS. 5*b* and 7 illustrate alternative uses of the discriminator function, it is also within the scope of the present invention to employ the discriminator function in response to both provisional detection of fibrillation and provisional detection of tachycardia. In such a case, it is anticipated that the parameters for the discriminator function may vary depending on whether tachycardia or fibrillation is provisionally detected.

While the preferred embodiment of the device takes the form of a microprocessor controlled device as illustrated in FIG. 4, in which the various functional steps illustrated in FIGS. 5*a*, 5*b*, 5*c*, 6 and 7 would be implemented in the form of software, the invention may equally well be practiced in the form of a dedicated, full custom digital integrated circuit or, even in the form of an analog circuit, employing analog values as substitutes for the digital values disclosed in conjunction with the above specification.

In addition, while the preferred embodiment disclosed above takes the form of a pacemaker/cardioverter/defibrillator, the enhanced ability to distinguish between various tachyarrhythmias are also valuable and applicable to devices which are only capable of performing a subset of the various therapies discussed above in conjunction with FIG. 4. For example, the ability to distinguish between a fast ventricular tachycardia and ventricular fibrillation is valuable in an implantable cardioverter defibrillator, even if the cardiac pacing function is omitted, as in the currently available CPI AICD implantable cardioverter defibrillators.

Further, the ability to distinguish between VT and rapid rhythms due to atrial fibrillation is similarly of value in the context of an antitachycardia pacer, even in the absence of high energy cardioversion and defibrillation therapies. It should further be kept in mind that while the therapies described for delivery in response to detection of the various arrhythmias discussed are all disclosed in the context of electrical therapies, it is possible that the invention may be embodied in the form of an implantable drug dispenser, wherein one or more of the anti-tachycardia therapies takes the form of injection of a drug locally into the heart or systemically to treat the detected arrhythmia. As such, the above disclosure should be taken merely as an example of an embodiment of the present invention, rather than limiting, when reading the claims which follow.

The preceding specific embodiments are illustrative of the practice of the invention. It is to be understood, therefore, that other expedients known to those of skill in the art or disclosed herein may be employed without departing from the invention or the scope of the appended claim. It is therefore to be understood that the invention may be practiced otherwise than is specifically described, without departing from the scope of the present invention. As to every element, it may be replaced by any one of infinite equivalent alternatives, only some of which are disclosed in the specification.

What is claimed is:

1. Apparatus for treating tachyarrhythmias, comprising:
   means for delivering a first therapy to a patient's heart to treat tachycardia and a second therapy to said patient's heart to treat fibrillation;
   means for sensing an electrical signal from said patient's heart indicative of a depolarization of a chamber or chambers of said patient's heart;
   means for measuring a time interval between depolarizations;
   means for storing the measured depolarization intervals;
   means for detecting an occurrence of a tachyarrhythmia based upon the measured depolarization intervals; and
   means responsive to the detection of an occurrence of a tachyarrhythmia for discriminating between tachycardia and fibrillation and for selecting between said first and second therapies;
   said discrimination and therapy selection means including:
   (i) means for sorting a predetermined number of the measured depolarization intervals into a plurality of interval range bins;
   (ii) means for determining the number of measured depolarization intervals within each of the interval range bins;
   (iii) means for defining a discrimination criterion based on determining whether designated ones of the plurality of interval range bins have at least a predetermined threshold number of measured depolarization intervals within them, wherein the threshold number is set as a value which decreases as a function of the length of the intervals between depolarizations; and
   (iv) means for triggering delivery of the first therapy if the discrimination criterion is met and for triggering delivery of the second therapy if the discrimination criterion is not met.

2. The apparatus of claim 1, wherein the discrimination criterion is used to distinguish between fast VT and VF, and if the discrimination criterion is met, the tachyarrhythmia is determined to be a fast ventricular tachycardia, the first therapy is delivered; and if the discrimination criterion is not met, the tachyarrhythmia is determined to be fibrillation and the second therapy is delivered.

3. The apparatus of claim 1, wherein the discrimination criterion is used to distinguish between VT and fast ventricular rhythms due to atrial fibrillation (VT vs. AF), and if the discrimination criterion is met, the tachyarrhythmia is determined to be a ventricular tachycardia and a tachycardia therapy is delivered; and if the discrimination criterion is not met, the tachyarrhythmia is determined to be due to atrial fibrillation and no therapy is delivered.

4. The apparatus of claim 1, wherein the predetermined threshold number of intervals required in order to meet the discrimination criterion is variable as a function of the underlying rate of the detected tachyarrhythmia.

5. The apparatus of claim 4, wherein the threshold number varies as a decreasing function of the tachyarrhythmia cycle lengths of a preceding series of depolarizations; and wherein the 75th percentile cycle length of the preceding sequence of depolarizations is employed as a measurement metric, with the threshold number of intervals expressed as a percentage of intervals binned decreasing from 100% to 30% in a linear fashion as the 75th percentile cycle length increases.

6. The apparatus of claim 5, wherein the 75th percentile cycle length of the preceding series of depolarizations is calculated by selecting the fourth longest interval out of the preceding twelve measured depolarization intervals.

7. Apparatus for treating tachyarrhythmias, comprising:
   means for delivering a first therapy to a patient's heart to treat tachycardia and a second therapy to said patient's heart to treat fibrillation;
   means for sensing an electrical signal from said patient's heart indicative of a depolarization of a chamber or chambers of said patient's heart;
   means for measuring a time interval between depolarizations;
   means for storing the measured depolarization intervals;
   means for detecting an occurrence of a tachyarrhythmia based upon the measured depolarization intervals; and
   means responsive to the detection of an occurrence of a tachyarrhythmia for discriminating between tachycardia and fibrillation and for selecting between said first and second therapies;
   said discrimination and therapy selection means including:
      (i) means for sorting a predetermined number of the measured depolarization intervals into a plurality of interval range bins;
      (ii) means for determining the number of measured depolarization intervals within each of the interval range bins;
      (iii) means for defining a discrimination criterion based on determining whether designated ones of the plurality of interval range bins have at least a predetermined threshold number of measured depolarization intervals within them, wherein the threshold number is set as a value which increases as an inverse function of a defined percentile of the length of intervals over a sequence of a predetermined number of intervals between depolarization; and
      (iv) means for triggering delivery of the first therapy if the discrimination criterion is met and for triggering delivery of the second therapy if the discrimination criterion is not met.

8. Apparatus for treating tachyarrhythmias, comprising:
   means for delivering a first therapy to a patient's heart to treat tachycardia and a second therapy to said patient's heart to treat fibrillation;
   means for sensing an electrical signal from said patient's heart indicative of a depolarization of a chamber or chambers of said patient's heart;
   means for measuring a time interval between depolarizations;
   means for storing the measured depolarization intervals;
   means for detecting an occurrence of a tachyarrhythmia based upon the measured depolarization intervals; and
   means responsive to the detection of an occurrence of a tachyarrhythmia for discriminating between tachycardia and fibrillation and for selecting between said first and second therapies;
   said discrimination and therapy selection means including:
      (i) means for sorting a predetermined number of the measured depolarization intervals into a plurality of interval range bins;
      (ii) means for determining the number of measured depolarization intervals within each of the interval range bins;
      (iii) means for defining a discrimination criterion based on determining whether designated ones of the plurality of interval range bins have at least a predetermined threshold number of measured depolarization intervals within them, wherein the threshold number is set as a value which increases as an inverse function of the 75th percentile of the length of intervals over a sequence of a predetermined number of intervals between depolarizations; and
      (iv) means for triggering delivery of the first therapy if the discrimination criterion is met and for triggering delivery of the second therapy if the discrimination criterion is not met.

* * * * *